United States Patent [19]

Goetz et al.

[11] 4,212,972
[45] Jul. 15, 1980

[54] PREPARATION OF CIS-2,6-DIMETHYLMORPHOLINE

[75] Inventors: Norbert Goetz, Worms; Walter Himmele, Walldorf; Leopold Hupfer, Friedelsheim, all of Fed. Rep. of Germany

[73] Assignee: BASF Aktiengesellschaft, Fed. Rep. of Germany

[21] Appl. No.: 40,200

[22] Filed: May 18, 1979

[30] Foreign Application Priority Data

Jul. 14, 1978 [DE] Fed. Rep. of Germany ....... 2830998

[51] Int. Cl.² ............................................. C07D 265/30
[52] U.S. Cl. .................................................. 544/106
[58] Field of Search .......................................... 544/106

[56] References Cited

U.S. PATENT DOCUMENTS 3,083,202  3/1963  Summers ............................... 544/106

OTHER PUBLICATIONS

Houben–Weyl "Met. der Org. Chemie" vol. 4/2 pp. 227–283.
Zelinsky et al. "Ber." vol. 65 (1932) p. 1613.

Primary Examiner—John M. Ford
Assistant Examiner—R. W. Ramsuer
Attorney, Agent, or Firm—Keil & Witherspoon

[57] ABSTRACT

A process for the preparation of cis-2,6-dimethylmorpholine from trans-2,6-dimethylmorpholine by isomerization over a catalyst in the presence of hydrogen.

2 Claims, No Drawings

PREPARATION OF CIS-2,6-DIMETHYLMORPHOLINE

The present invention relates to a process for the preparation of cis-2,6-dimethylmorpholine from trans-2,6-dimethylmorpholine by isomerization over a catalyst in the presence of hydrogen.

U.S. Pat. No. 3,083,202 discloses that in a mixture of cis- and trans-2,6-dimethylmorpholine the proportion of the cis-compound can be increased by heating the mixture with concentrated or fuming sulfuric acid at from 185° to 220° C. It is also known that in some cases cis-/trans isomerizations can be carried out over hydrogenation catalysts (Houben-Weyl, "Methoden der organischen Chemie", volume 4/2, pages 227 to 283). For example, cis-1,4-dimethylcyclohexane can be isomerized to trans-1,4-dimethylcyclohexane in the presence of a nickel catalyst at 175° C. [N. D. Zelinsky and E. J. Margolis, Ber. dtsch. chem. Ges. 65, (1932), 1613].

We have found that cis-2,6-dimethylmorpholine of the formula I

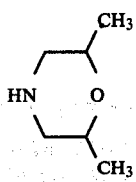

is obtained in a simple manner if trans-2,6-dimethylmorpholine of the formula II

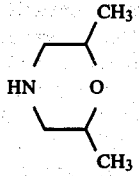

is isomerized in the presence of hydrogen and of a catalyst which contains one or more metals of group VIII or group Ib of the periodic table of the elements, or mixtures of such metals.

The advantage of the process according to the invention is that cis-2,6-dimethylmorpholine is obtained substantially free from by-products and waste products. By contrast, the conventional isomerization with sulfuric acid leads, on subsequent neutralization of the mixture with alkalis and liberation of the 2,6-dimethylmorpholine base, to polluting compounds, in the form of undesired alkali metal sulfates, which must be discharged into rivers.

Cis/trans isomerizations of appropriately substituted morpholine rings in the presence of hydrogenation catalyts have not previously been disclosed.

The isomerization according to the invention can be carried out continuously or batchwise. As a rule, it is carried out at from 120° to 280° C., advantageously from 150° to 250° C., under pressures of from 1 to 200 bar, advantageously from 1 to 50 bar. The isomerization can be carried out in the absence of any solvents or in the presence of solvents which are inert under the reaction conditions.

Examples of suitable solvents are cyclohexane, cyclopentane, methylcyclopentane, hexane, heptane, cyclohexyl methyl ether, di-n-butyl ether, tetrahydrofuran and dioxane.

Suitable catalysts are nickel, cobalt, copper, silver and especially palladium catalysts. These may be employed in the pure form, ie. purely as one metal, or in the form of mixed catalysts, with or without carriers. Examples of suitable inert carriers are active charcoal, $SiO_2$ and $Al_2O_3$. The addition of a basic metal oxide, for example an oxide of one of the rare earth metals, eg. $Pr_2O_3$, $La_2O_3$, $CeO_2$, $Nd_2O_3$, $Gd_2O_3$ or $Sm_2O_3$, is very advantageous.

The catalyst for example contains from 0.1 to 98% by weight of metal.

In general, the catalyst is used in the form of tablets, preferably of from 4 to 5 mm diameter, or in the form of a powder.

Cis-2,6-dimethylmorpholine prepared according to the process of the invention is used as an intermediate for the preparation of fungicidal active ingredients for plant protection agents (German Laid-Open Application DOS 2,656,747).

In the Examples which follow, parts are by weight and bear the same relation to parts by volume at that of the kilogram to the liter.

EXAMPLE 1

1,500 parts by weight of trans-2,6-dimethylmorpholine are introduced into a rolling autoclave of capacity 3,000 parts by volume. 5 parts by weight of 10% strength palladium on active charcoal are added as the catalyst. The autoclave is sealed pressure-tight and is next flushed with nitrogen. 10 bar pressure of hydrogen are then forced in and released again. The autoclave is then heated to 175° C. and kept at this temperature for 36 hours. A sample of the reaction mixture taken after this reaction time contains, according to gas-chromatographic analysis, 53.5% of cis-2,6-dimethylmorpholine and 46.3% of trans-2,6-dimethylmorpholine. After a further 36 hours' reaction time at 175° C., the proportion of the cis-compound rises to 70.6% whilst the proportion of the trans-compound drops to 29.2%.

Fractionation of the reaction through a distillation column with about 60 theoretical plates gives 810 parts of pure cis-2,6-dimethylmorpholine, boiling point 80°–81° C./100 mm Hg. This corresponds to a yield of 54% (without taking into account the trans-2,6-dimethylmorpholine which can be recycled). In addition, 531 parts of a fraction consisting predominantly of trans-2,6-dimethylmorpholine, boiling point 87°–90° C./100 mm Hg, are obtained. 158 parts of higher-boiling products (distillation residue) are also obtained. The selectivity of the reaction is 89.5%.

EXAMPLE 2

Using the method described in Example 1, 1,500 parts of trans-2,6-dimethylmorpholine are treated for 24 hours at 200° C. in the presence of 5 parts of the catalyst described in Example 1 and in the presence of hydrogen. After this reaction time, gas-chromatographic analysis shows the presence of 80% of cis-compound and 20% of trans-compound. Fractionation of the reaction product gives 965 parts of pure cis-2,6-dimethylmorpholine. This corresponds to a yeild of 64.5% (without taking account of the recoverable starting material trans-2,6-dimethylmorpholine). 408 parts of trans-2,6-dimethylmorpholine are obtained. The distillation residue amounts to 126 parts. The selectively achieved is 91.5%.

EXAMPLE 3

1,500 parts of trans-2,6-dimethylmorpholine are isomerized in the presence of 2 parts of the catalyst described in more detail in Example 1, at 225° C. In other respects, the reaction conditions described iin detail in Example 1 are used.

Samples of about 150 parts of reaction product are taken at 6 hour intervals. The composition of these samples is analyzed by gas chromatography, and the distillation residue is determined. For the latter purpose, the products distillable at up to 205° C. are distilled off. The composition of the distillate is again determined by gas chromatography. The analytical values obtained are listed in the Table which follows:

| Reaction time in hours | Proportion of cis-compound in the crude product | Proportion of trans-compound in the crude product | Proportion of cis-compound in the distillate | Proportion of trans-compound in the distillate | % by weight of distillation residue |
|---|---|---|---|---|---|
| 6  | 31.4 % | 68.2 % | 30.1 % | 68.7 % | 8.5 % |
| 12 | 51.8 % | 48.1 % | 51.3 % | 47.1 % | 10.4 % |
| 18 | 63.0 % | 27.7 % | 61.5 % | 35.1 % | 12.1 % |
| 24 | 76.3 % | 22.6 % | 74.3 % | 25.1 % | 15.2 % |

EXAMPLE 4

A rolling autoclave having a capacity of 1,000 parts by volume is charged with a mixture of 100 parts of trans-2,6-dimethylmorpholine, 500 parts of tetrahydrofuran and 25 parts of a catalyst which consists of 7.9% by weight of nickel, 7.9% by weight of cobalt and 3.2% by weight of copper on aluminum oxide. After flushing with nitrogen, hydrogen is forced in until the pressure reaches 10 bar. The autoclave is then heated to 170° C. and is kept at this temperature for 10 hours. Thereafter it is cooled, the catalyst is filtered off and the filtrate is purified by distillation. This gives 91 parts of a mixture which consists of 89% of 2,6-dimethylmorpholine, the latter comprising 51% of cis-compound and 49% of trans-compound. 9 parts of distillation residue are obtained. From the above, the selectivity is calculated to be 81%.

EXAMPLE 5

A catalyst, composed of 91% by weight of cobalt, 5% by weight of manganese and 4% by weight of $H_3PO_4$, in the form of extrudates of 5 mm diameter and 10 mm length, is introduced into a cylindrical reaction tube having a capacity of 500 parts by volume, and is heated to 170° C. Per hour, 60 parts of trans-2,6-dimethylmorpholine are passed over this catalyst bed. At the same time, 10,000 parts by volume of hydrogen under a pressure of 50 bar are passed through the tube in co-current. The reaction product issuing from the reaction tube is cooled under pressure and then let down. This gives 60 parts per hour of a crude product, which is purified by distillation. A sample distillation of 100 parts of the crude product, carrier out similarly to the sample distillation described under Example 3, gives the following results; the distillate (98 parts) contains 58.5% of cis-2,6-dimethylmorpholine and 31.5% of trans-2,6-dimethylmorpholine. The distillation residue amounts to 1.5%. This indicates a selectivity of 88%.

EXAMPLE 6

A catalyst comprising 0.36% by weight of palladium, 4.8% by weight of silver and 1% by weight of manganese on $SiO_2$, in the form of extrudates of 5 mm diameter and 10 mm length, is filled into the apparatus described in more detail in Example 5, and is heated to 250° C. 60 parts per hour of trans-2,6-dimethylmorpholine are passed over this catalyst and at the same time 10,000 parts by volume of hydrogen are passed through the apparatus in co-current under a pressure of 50 bar. The reaction product issuing from the reaction tube is cooled under pressure and then let down. 60 parts per hour of a crude product are obtained and are purified by distillation.

A sample distillation of 100 parts of the crude product, carried out under the conditions described in Example 3, gives the following results: the distillate contains 32% of cis-2,6-dimethylmorpholine and 68% of trans-2,6-dimethylmorpholine. The distillation residue amounts to 11.5%. From these data, the selectivity is calculated to be 88%.

EXAMPLE 7

A catalyst consisting of 0.5% by weight of palladium and 5% by weight of praseodymium oxide, $Pr_2O_3$, on aluminum oxide as the carrier, the catalyst being in the form of extrudates of 5 mm diameter and 10 mm length, is introduced into the apparatus described in more detail in Example 5, and is heated to 230° C. Per hour, 60 parts of trans-2,6-dimethylmorpholine and, at the same time, 10,000 parts by volume of hydrogen under a pressure of 50 bar are passed over this catalyst. The product issuing from the reaction tube is cooled under pressure and then let down. 60 parts per hour of a crude product are obtained and are purified by distillation. A sample distillation of 100 parts of the crude product gives the following results: the distillate (97 parts) contains 73% of cis-2,6-dimethylmorpholine and 24% of trans-2,6-dimethylmorpholine. The distillation residue amounts to 2.5%. The selectivity is calculated to be 94%.

EXAMPLE 8

The isomerization of trans-2,6-dimethylmorpholine is carried out at 250° C., using the apparatus described in Example 5 and the catalyst described in Example 7. All other conditions are identical to those of Example 7. In this case, the sample distillation of 100 parts of crude product gives the following values: the distillate (95 parts) contains 82.5% of cis-2,6-dimethylmorpholine and 14.5% of trans-2,6-dimethylmorpholine. The distillation residue amounts to 4%. From the above data, the selectivity is calculated to be 94%.

We claim:

1. A process for the preparation of cis-2,6-dimethylmorpholine by isomerizing trans-2,6-dimethylmorpholine, wherein trans-2,6-dimethylmorpholine is isomerized in the presence of hydrogen and of a catalyst which contains one or more metals of group VIII or group Ib of the periodic table of the elements, or contains a mixture of these, at from 120° to 280° C., especially from 150° to 250° C., under a pressure of from 1 to 200 bar.

2. A process as claimed in claim 1, wherein the catalyst contains palladium.

* * * * *